(12) United States Patent
Shimada

(10) Patent No.: US 9,186,845 B2
(45) Date of Patent: Nov. 17, 2015

(54) WEB WELDING SYSTEM AND WELDING METHOD

(71) Applicant: Takahiro Shimada, Osaka (JP)

(72) Inventor: Takahiro Shimada, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 0 days.

(21) Appl. No.: 14/439,633

(22) PCT Filed: Nov. 5, 2013

(86) PCT No.: PCT/JP2013/079842
§ 371 (c)(1),
(2) Date: Apr. 29, 2015

(87) PCT Pub. No.: WO2014/077152
PCT Pub. Date: May 22, 2014

(65) Prior Publication Data
US 2015/0298390 A1  Oct. 22, 2015

(30) Foreign Application Priority Data

Nov. 13, 2012  (JP) ................. 2012-249097

(51) Int. Cl.
| B32B 37/00 | (2006.01) |
| B29C 65/08 | (2006.01) |
| B29C 65/78 | (2006.01) |
| B29K 101/12 | (2006.01) |
| B29K 105/00 | (2006.01) |

(52) U.S. Cl.
CPC ............. *B29C 65/08* (2013.01); *B29C 65/7894* (2013.01); *B29K 2101/12* (2013.01); *B29K 2105/256* (2013.01)

(58) Field of Classification Search
CPC .... B29C 65/08; B29C 65/7894; B29C 66/431
USPC ................... 156/73.1, 290, 555, 580.1, 580.2
See application file for complete search history.

(56) References Cited

U.S. PATENT DOCUMENTS

| 4,713,132 | A | * | 12/1987 | Abel | B29C 65/087 156/290 |
| 4,758,293 | A | * | 7/1988 | Samida | B29C 65/08 156/308.4 |
| 5,660,679 | A | * | 8/1997 | Rajala | B29C 66/431 156/580.1 |
| 5,817,199 | A | * | 10/1998 | Brennecke | B29C 65/087 156/290 |
| 7,325,373 | B2 | * | 2/2008 | Boldrini | B29C 65/081 156/73.1 |
| 7,449,084 | B2 | * | 11/2008 | Nakakado | A61F 13/15739 156/580.1 |
| 8,074,693 | B2 | * | 12/2011 | Yamamoto | A61F 13/15723 156/510 |
| 2007/0251643 | A1 | * | 11/2007 | Umebayashi | A61F 13/15739 156/350 |
| 2008/0236756 | A1 | | 10/2008 | Nakakado | |

FOREIGN PATENT DOCUMENTS

| JP | 2001-506945 A | 5/2001 |
| WO | WO 2005/080065 A1 | 9/2005 |

OTHER PUBLICATIONS

International Search report for corresponding International Application No. PCT/JP2013/079842 mailed Jan. 28, 2014.

* cited by examiner

*Primary Examiner* — James Sells
(74) *Attorney, Agent, or Firm* — Renner, Otto, Boisselle & Sklar, LLP

(57) ABSTRACT

First and second anvil rolls (10A, 10B) are arranged so that in the welding of webs, the webs are transported to pass through a first gap ($\Delta 1$) between the first anvil roll (10A) and a first horn (21), a third gap ($\Delta 3$) between the second anvil roll (10B) and a third horn (23), a fourth gap ($\Delta 4$ between the second anvil roll (10B) and the fourth horn (24) and a second gap ($\Delta 2$) between the first anvil roll (10A) and the second horn (22) in this order.

6 Claims, 4 Drawing Sheets

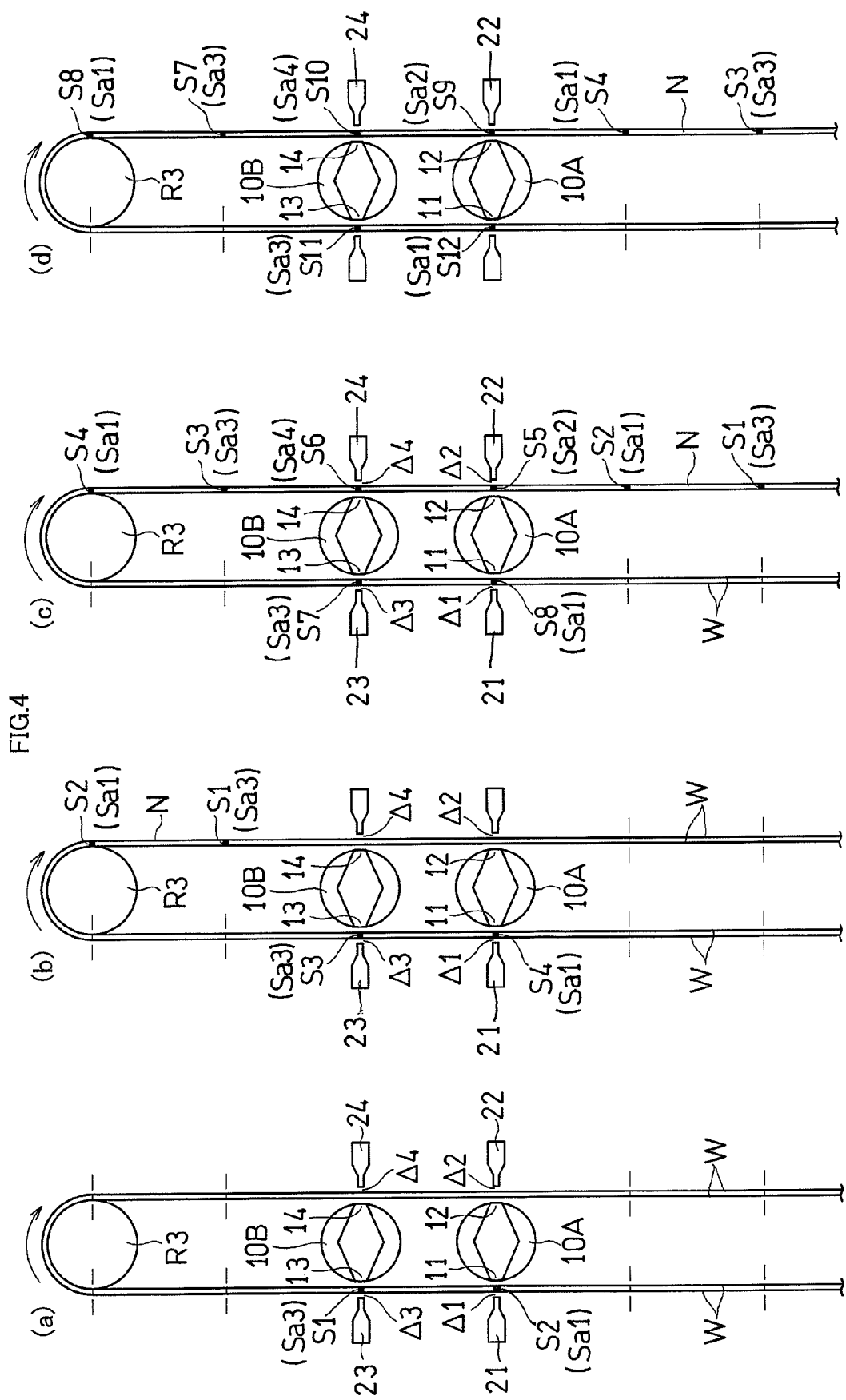

WEB WELDING SYSTEM AND WELDING METHOD

TECHNICAL FIELD

The present invention relates to a web welding system and a welding method mainly for a wearing article.

BACKGROUND ART

For example, a welding system is known in which in order to seal (weld) a continuous laminate for each unit of disposable pants, a pair of ultrasonic horns and a pair of anvils are provided (WO05/080065A1).

In this conventional art, continuous webs are reversed with a reverse roll, and an anvil roll is provided that has a pair of anvils which can make contact with the webs in both upstream and downstream sides with respect to the reverse roll. With the ultrasonic horn corresponding to each of the anvils, seal processing is performed on the webs before and after the webs pass the reverse roll.

CITATION LIST

Patent Literature

[First Patent Document] WO05/080065A1

SUMMARY OF INVENTION

In the conventional art, a pair of horns are operated simultaneously, and thus a load on the anvil roll is reduced and the accuracy of a welding position is enhanced.

However, the conventional art neither discloses nor suggests that a plurality of anvil rolls is provided.

An object of the present invention is to provide a web welding system and a web welding method that each reduces a time necessary for welding and that each can increase the speed of welding.

A device according to the present invention includes: a first anvil roll that includes a pair of anvils; first and second ultrasonic horns that work together with the pair of anvils to apply vibration energy (energies) to the webs; a second anvil roll that includes another pair of anvils; and third and fourth ultrasonic horns that work together with the pair of anvils in the second anvil roll to apply vibration energy (energies) to the webs, where the first and second ultrasonic horns are arranged so that any one of the pair of anvils in the first anvil roll is opposite to the first horn and that simultaneously, the other of the pair of anvils in the first anvil roll can be opposite to the second horn, the third and fourth ultrasonic horns are arranged so that any one of the pair of anvils in the second anvil roll is opposite to the third horn and that simultaneously, the other of the pair of anvils in the second anvil roll can be opposite to the fourth horn, and the first and second anvil rolls are arranged so that the webs are transported (transferred) to pass through a first gap between the first anvil roll and the first horn, a third gap between the second anvil roll and the third horn, a fourth gap between the second anvil roll and the fourth horn, and a second gap between the first anvil roll and the second horn, in this order.

In the present invention, a pair of anvils are respectively provided for a pair of anvil rolls, and ultrasonic welding is simultaneously performed with four horns (at least two) that work together with the anvils. Hence, the time necessary for the welding can be reduced.

A method of welding webs using the device according to the present invention includes: a step of transporting (transferring) the webs so that the webs pass through the first gap, the third gap, the fourth gap, and the second gap, in this order; a step of ultrasonic-welding a first part and a second part of the webs with the third and first horns, respectively; a step of ultrasonic-welding a third part and a fourth part of the webs, on a downstream side with respect to the second part, with the third and first horns, respectively; and a step of ultrasonic-welding a fifth part and a sixth part of the webs, between the second part and the third part, with the second and fourth horns, respectively.

In this case, the third and first horns weld the first part and the second part, after the transport (transfer) of the webs, the third and first horns weld the third part and the fourth part on the downstream side with respect to the second part, and thereafter the second and fourth horns weld the fifth part and the sixth part between the second part and the third part.

In other words, until the third part and the fourth part are welded since the third and first horns have welded the first part and the second part, the webs can be transported (transferred) by skipping the parts in two places to be welded (the fifth part and the sixth part to be welded by the second and fourth horns on the downstream side). Hence, it is possible to increase the speed of the welding.

BRIEF DESCRIPTION OF DRAWINGS

FIGS. 4(a) to 4(d) are conceptual diagrams each showing welding steps in the present invention.

DESCRIPTION OF EMBODIMENTS

Figure 1:
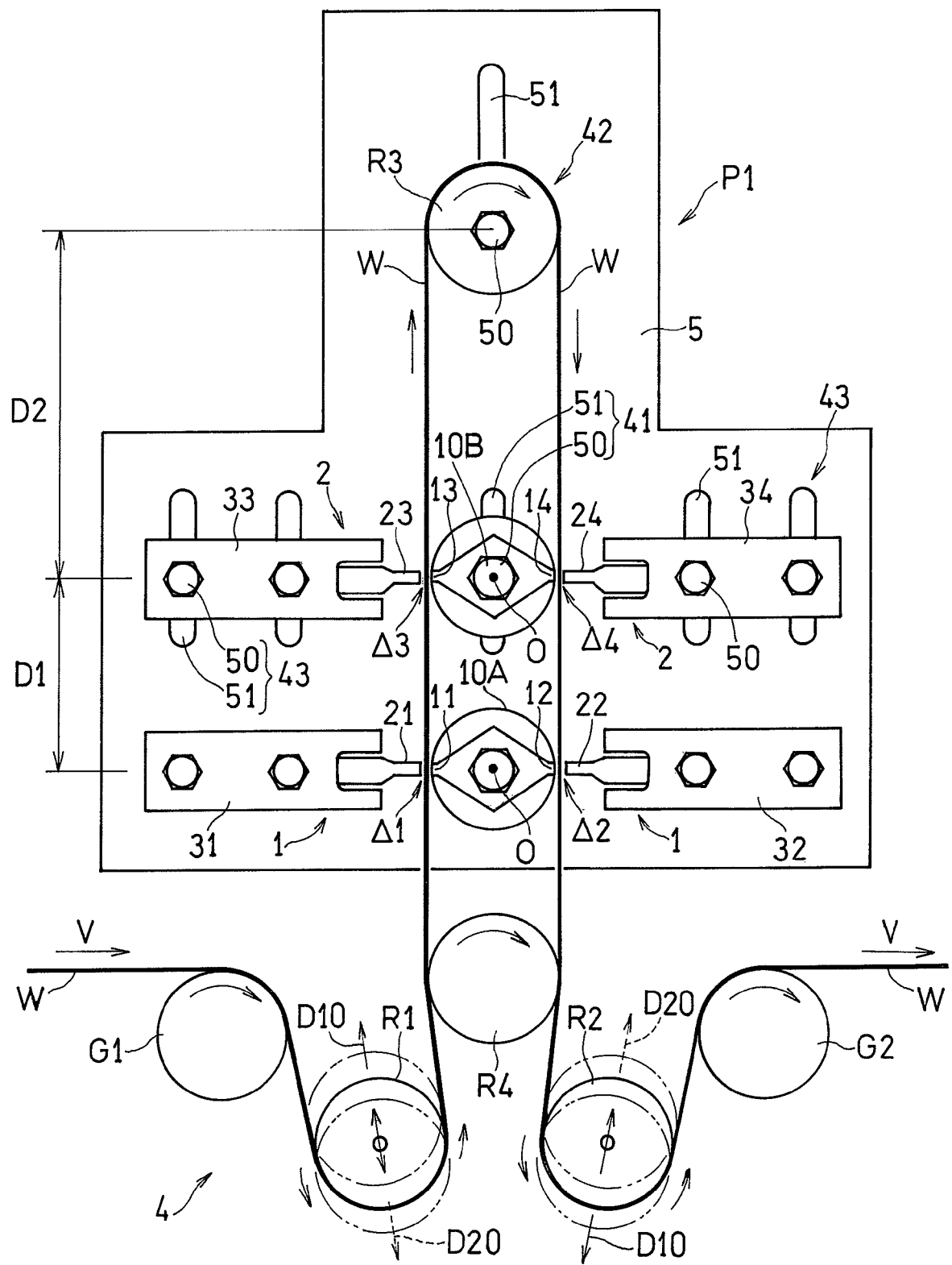
FIG. 1 is a schematic configuration diagram showing a welding system when a wearing article of a medium size is manufactured in an embodiment of the present invention.

Preferably, the web welding system according to the present invention further includes a first size adjustment means that can change (adjust) a first distance between the first anvil roll and the second anvil roll. The first distance means the distance between the axis lines of both the anvil rolls.

The first distance between both the anvil rolls can be changed, and thus it is possible to change sizes such as a small size, a medium size and a large size in for example, a wearing article.

Further preferably, the system according to the present invention further includes a reverse roll that is arranged on the side of the second anvil roll opposite to the first anvil roll and that reverses the direction of the webs passing through the third gap toward the fourth gap; and a second size adjustment means that can change (adjust) a second distance between the second anvil roll and the reverse roll. The second distance means the distance between the axis lines of the second anvil roll and the reverse roll.

The second distance between the second anvil roll and the reverse roll can be changed, and thus it is possible to easily perform the size change described above.

Further preferably, the pair of anvils in the first anvil roll are provided symmetrically with respect to an axis line of the first anvil roll, and the pair of anvils in the second anvil roll are provided symmetrically with respect to an axis line of the second anvil roll.

In the present system, for each anvil roll, the webs are simultaneously welded at two places. Here, the anvil roll simultaneously receives two forces of opposite directions toward the approximate center of the anvil roll through the webs from the ultrasonic horn.

The anvil roll simultaneously receives two forces of opposite directions, and thus a load on the anvil roll caused by an impact of ultrasonic energy is reduced, and even when vibration energy is applied by the ultrasonic horn to the anvil roll, variations in the position (positional displacement) of the anvil are unlikely to be occurred. Hence, the accuracy of the position in the welding is enhanced.

Preferably, the welding system further includes a transport (transfer) device that introduces the webs into the first gap and receives the webs from the second gap. The device repeatedly performs high-speed transport and low-speed transport of the webs in a predetermined period. The welding method further includes a step of repeatedly performing the high-speed transport of the webs and the low-speed transport of the webs with assumption that a length four times as long as a pitch of weldings determined by a first distance between the first gap and the third gap is one period, and the ultrasonic-welding steps are performed when the low-speed transport is performed.

In this case, since the high-speed transport and the low-speed transport of the webs are repeatedly performed with assumption that a length of a part of the webs four times as long as the pitch to be welded is one period in the transport, it is possible to reduce the time during which the low-speed transport is performed, with the result that it is possible to enhance the production speed.

Since the present system has the four ultrasonic horns, even when it is assumed that the length of the part of the webs four times as long as the pitch is one period in the transport, it is possible to weld the webs with the predetermined pitch.

Embodiment

The present invention will be clearly understood from the following description of a preferred embodiment with reference to accompanying drawings. However, the embodiment and the drawings are intended simply for illustration and description, and should not be utilized for determining the scope of the present invention. The scope of the present invention is determined only by the scope of claims. In the accompanying drawings, the same component numbers in a plurality of drawings represent the same or corresponding parts.

The embodiment of the present invention will be described below with reference to the drawings.

In the following description, the main portions of a welding system according to the present invention will first be described, and a speed change device provided in the welding system will then be described.

The present system includes a pair of first and a pair of second ultrasonic welding devices 1 and 2 that weld together a plurality of webs W overlaid on each other, while the system transporting (transferring) the webs W. The first and second ultrasonic welding devices 1 and 2 are separate from each other in the direction of flow of the webs W.

The first ultrasonic welding device 1 includes: a first anvil roll 10A that has a pair of anvils 11 and 12; first and second ultrasonic horns 21 and 22 that work together with the pair of anvils 11 and 12 to apply vibration energy to the webs W; and first and second sonic main bodies 31 and 32 that produce ultrasonic vibrations in the ultrasonic horns 21 and 22, respectively.

The second ultrasonic welding device 2 includes: a second anvil roll 10B that has another pair of anvils 13 and 14; third and fourth ultrasonic horns 23 and 24 that work together with the pair of anvils 13 and 14 to apply vibration energy to the webs W; and third and fourth sonic main bodies 33 and 34 that produce ultrasonic vibrations in the ultrasonic horns 23 and 24, respectively.

Mechanical vibrations having a high frequency are applied to the horns 21 to 24, and thus the plurality of webs W passing between the ultrasonic horns 21 to 24 and the anvils 11 to 14 are weld together with frictional heat.

As the ultrasonic horns 21 to 24, for example, ultrasonic horns disclosed in Japanese Unexamined Patent Application Publication (Translation of PCT Application) No. 10-513128 may be used. As already known, in the surfaces of the horns 21 to 24, for example, a seal pattern consisting of a large number of convex portions may be formed.

Instead of forming the seal pattern in the surface of the horns 21 to 24, a seal pattern may be formed in the surface of the anvils 11 to 14.

The webs W are formed by overlaying a plurality of thermoplastic webs which are necessary to weld each other. The welded regions Sa1, Sa2, Sa3, and Sa4 that are sealed with the first and second ultrasonic welding devices 1 and 2 are, for example, end portions of products such as disposable pants (an example of a wearing article) shown in FIGS. 3(a) to 3(c).

The pitch between the welded regions Sa1, Sa2, Sa3, and Sa4 is set at predetermined pitches Spm and Spl for medium and large sizes, respectively.

For example, the pair of anvils 11 and 12 of the first anvil roll 10A in FIG. 1 are provided symmetrically with respect to the axis line (line extending along the rotation center O of the first anvil roll 10A) of the first anvil roll 10A. In other words, the pair of anvils 11 and 12 are provided in the first anvil roll 10A with a pitch of 180°.

For example, the first ultrasonic horn 21 and the second ultrasonic horn 22 are arranged symmetrically with the rotation center (the axis line described above) O of the first anvil roll 10A in the center.

In other words, the pair of ultrasonic horns 21 and 22 is arranged so that when one of the pair of anvils 11 and 12 is opposite to the first ultrasonic horn 21, the other one of the pair of anvils 11 and 12 can be simultaneously opposite to the second ultrasonic horn 22.

For example, the pair of anvils 13 and 14 of the second anvil roll 10B are provided symmetrically with respect to the axis line (line extending along the rotation center O of the second anvil roll 10B) of the second anvil roll 10B. In other words, the pair of anvils 13 and 14 are provided in the second anvil roll 10B with a pitch of 180°.

For example, the third ultrasonic horn 23 and the fourth ultrasonic horn 24 are arranged symmetrically with the rotation center O of the second anvil roll 10B in the center.

In other words, the pair of ultrasonic horns 23 and 24 is arranged so that when one of the pair of anvils 13 and 14 is opposite to the third ultrasonic horn 23, the other one of the pair of anvils 13 and 14 can be simultaneously opposite to the fourth ultrasonic horn 24.

With each of the pair of anvils 11 and 12 of the first anvil roll 10A opposite to the first ultrasonic horn 21 or the second ultrasonic horn 22 and with each of the other pair of anvils 13 and 14 of the second anvil roll 10B opposite to the third ultrasonic horn 23 or the fourth ultrasonic horn 24, the ultrasonic horns 21 to 24 simultaneously apply vibration energy to the webs W. Hence, for each of the anvil rolls 10A and 10B, the webs W are simultaneously welded at two places.

Here, each of the anvil rolls 10A and 10B simultaneously receives two forces of opposite directions toward the centers O of the anvil rolls 10A and 10B through the webs W from the ultrasonic horns 21 to 24.

As described above, since the anvil rolls 10A and 10B simultaneously receive the forces of opposite directions, even when the ultrasonic horns 21 to 24 apply large vibration energy to the anvil rolls 10A and 10B, variations in the position (positional displacement) of the anvils 11 to 14 are unlikely to be occurred.

In each of the anvil rolls 10A and 10B, in addition to the pair of anvils, another pair or a plurality of pairs of anvils may be provided.

The first and second anvil rolls 10A and 10B are arranged so that the webs are transported in the following order: a first gap Al between the first anvil roll 10A and the first horn 21, a third gap Δ3 between the second anvil roll 10B and the third horn 23, a fourth gap Δ4 between the second anvil roll 10B and the fourth horn 24, and a second gap Δ2 between the first anvil roll 10A and the second horn 22.

The present system includes a transport device (transporting means) 4. The transport device 4 has a reverse roll R3 on the side of the second anvil roll 10B opposite to the first anvil roll 10A. The reverse roll R3 reverses the direction of the webs passing through the third gap Δ3 toward the fourth gap Δ4.

The webs W are passed from the first gap Al through the third gap Δ3 to the reverse roll R3. After flown along the outer circumferential surface of the reverse roll R3, the webs W are thereafter passed through the fourth gap Δ4 and are transported to the second gap Δ2.

In the present system, the first and second ultrasonic welding devices 1 and 2, the transport device 4 and the like are arranged so that an arrangement thereof in the upstream side and an arrangement thereof in the downstream side are substantially symmetrical with respect to a plane.

The present system includes first to third size adjustment means 41 to 43.

The first size adjustment means 41 can change a first distance (pitch) D1 between the first anvil roll 10A and the second anvil roll 10B.

The second size adjustment means 42 can change a second distance (pitch) D2 between the second anvil roll 10B and the reverse roll R3.

The third size adjustment means 43 can change a distance D1 between the first ultrasonic welding device 1 and the second ultrasonic welding device 2.

The second distance D2 means the distance between the shaft centers of the reverse roll R3 and the second anvil roll 10B, and the first distance D1 means the distance between the shaft centers of the second anvil roll 10B and the first anvil roll 10A.

The reverse roll R3 and the first and second anvil rolls 10A and 10B are rotatably attached to a frame 5 via an attachment unit 50. The reverse roll R3, the second anvil roll 10B, and the third and fourth sonic main bodies 33 and 34 are attached to the frame 5 via a long hole 51 formed in the frame 5 so that an attachment position in the direction of flow of the webs W can be changed.

The long hole 51 extends along the direction of flow of the webs W.

Figure 3A:
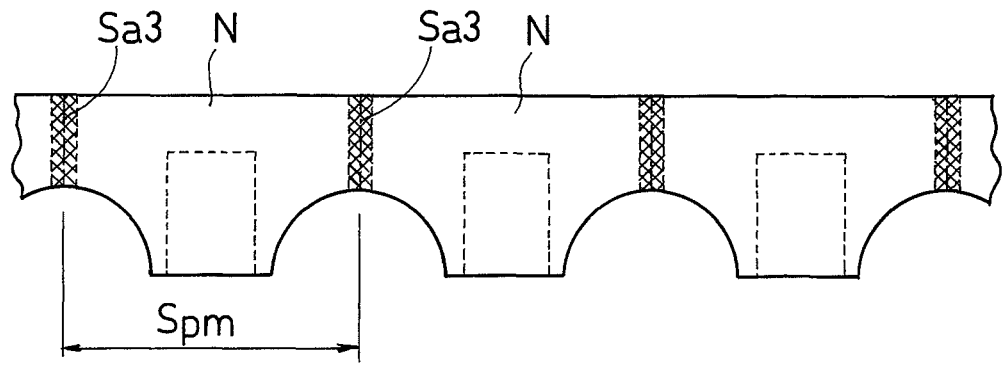
FIGS. 3(a) to 3(c) are schematic front views each showing an example of a wearing article before it is cut into individual products.
Figure 3B:
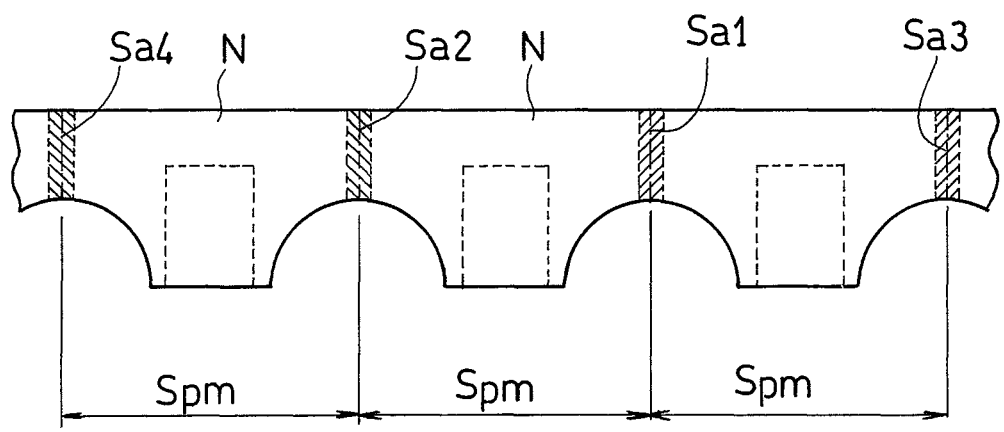

When a wearing article of a first size (for example, medium size) in FIGS. 3(a) and 3(b) is manufactured, the reverse roll R3, the second anvil roll 10B, and the third and fourth sonic main bodies 33 and 34 are supported by the first to third size adjustment means 41 to 43 of FIG. 1 in the first position P1 shown in FIG. 1.

Figure 2:
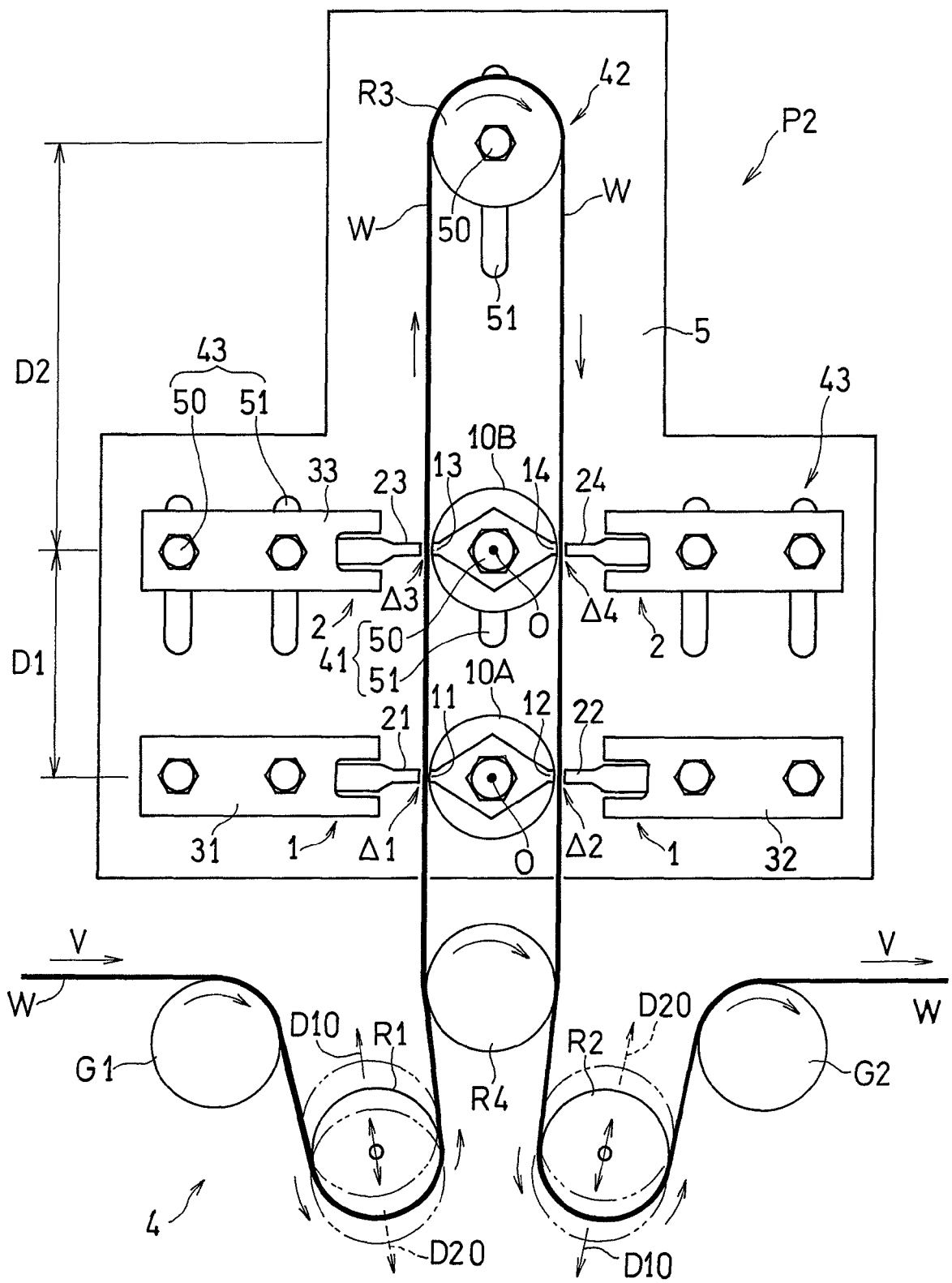
FIG. 2 is a schematic configuration diagram showing a welding system when a wearing article of a large size is manufactured.
Figure 3C:
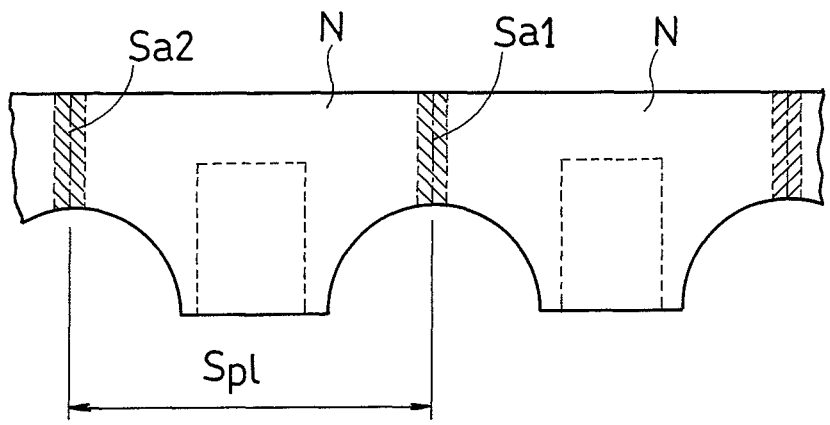

On the other hand, when a wearing article of a second size (for example, large size) in FIG. 3(c) is manufactured, the reverse roll R3, the second anvil roll 10B, and the third and fourth sonic main bodies 33 and 34 are supported by the first to third size adjustment means 41 to 43 of FIG. 2 in the second position P2 shown in FIG. 2.

In other words, as compared with the first distance D1 and the second distance D2 shown in FIG. 1, the first distance D1 and the second distance D2 shown in FIG. 2 are larger than them.

The welded regions Sa1, Sa2, Sa3, and Sa4 of a wearing article N in FIGS. 4(a) to 4(d) are welded when the webs W are passed through the first to fourth gaps Δ1 to Δ4 in FIG. 1.

On the other hand, the welding described above is simultaneously performed in the first to fourth gaps Δ1 to Δ4.

Thus, the length of the part of the webs W from the first gap Δ1 to the third gap Δ3 (or the length of the part from the second gap Δ2 to the fourth gap Δ4), that is, the first distance D1 needs to be set at an integral multiple of the pitch Spm or Spl of the wearing article N in FIGS. 3(a) to 3(c).

Hence, as described above, the reverse roll R3 and the first and second ultrasonic welding devices 1, 2 in FIG. 1 are selectively supported in one of the first position P1 and the second position P2, with the result that it is possible to manufacture wearing articles in two or more sizes.

The speed change device 4 includes a first dancer roller R1, a second dancer roller R2, a drive roller R4, and a plurality of guide rollers G1 and G2. The first dancer roller R1 of FIG. 1 receives the webs W flowing in from the upstream side, and discharges the webs W toward the first gap Δ1. The second dancer roller R2 receives the webs W discharged from the second gap Δ2, and discharges the webs W toward the downstream side.

The first and second dancer rollers R1 and R2 reciprocate (swing) as indicated by imaginary lines and solid lines. The first and second dancer rollers R1 and R2 are rotated at the same rotation speed (circumferential speed) by an unillustrated drive means.

On the upstream side of the first dancer roller R1, the first guide roller G1 is rotatably provided. On the other hand, on the downstream side of the second dancer roller R2, the second guide roller G2 is rotatably provided.

The first guide roller G1 guides the webs W flowing toward the first dancer roller R1. On the other hand, the second guide roller G2 guides the webs W flowing from the second dancer roller R2.

In a position above the area between both the dancer rollers R1 and R2, the drive roller R4 is arranged. The five rollers R1, R2, G1, G2, and R4 shown in FIGS. 1 and 2 are rotated in synchronization with one another.

The drive device for the five rollers is disclosed in WO2005/080065A1, and all the description thereof is incorporated herein.

Between the two dancer rollers R1 and R2, the speed change device 4 alternately repeats high-speed transport and low-speed transport of the webs W. In the high-speed transport, the movement speed of the webs W between the dancer rollers R1 and R2 is higher than the speed V of the webs W flowing into the first dancer roller R1.

On the other hand, in the low-speed transport, the movement speed of the webs W between the dancer rollers R1 and R2 is lower than the speed V.

In other words, in the high-speed transport, as indicated by a solid arrow D10, both the dancer rollers R1 and R2 are moved so that the first dancer roller R1 approaches the first anvil roll 10A and, at the same time, the second dancer roller R2 is moved away from the first anvil roll 10A, with the result that the webs W are transported at a high speed between both the dancer rollers R1 and R2.

On the other hand, in the low-speed transport, as indicated by a broken line arrow D20, both the dancer rollers R1 and R2 are moved so that the first dancer roller R1 is moved away from the first anvil roll 10A and, at the same time, the second dancer roller R2 approaches the first anvil roll 10A, with the result that the webs W are transported at a low speed between both the dancer rollers R1 and R2.

When the anvils 11 to 14 are respectively opposite to the ultrasonic horns 21 to 24, a control device (not shown) performs control such that the speed of the webs W between the first dancer roller R1 and the second dancer roller R2 is lower than the speed V of the webs W flowing into the first dancer roller R1, and the welding using ultrasonic energy is performed.

On the other hand, when the anvils 11 to 14 are not opposite to the ultrasonic horns 21 to 24, the control device (not shown) performs control such that the speed V of the webs W between the first dancer roller R1 and the second dancer roller R2 is higher than the speed V of the webs W flowing into the first dancer roller R1.

Both the dancer rollers R1 and R2 repeatedly reciprocate (swing) in the direction of the arrows D10 and D20, and thus the high-speed transport and the low-speed transport are repeated.

As described above, when the ultrasonic horns 21 to 24 apply the vibration energy to the webs W, the speed of the webs W that are passed between the ultrasonic horns 21 to 24 and the anvils 11 to 14 is low. Hence, the time during which the webs W receive the vibration energy is increased, and the energy per unit area applied to the webs W is increased. Consequently, the reliability of the welding is enhanced.

The operation of the present system will then be described.

The webs W of FIG. 1 flow at a substantially constant speed V from the first guide roller G1 to the first dancer roller R1. After flown along the outer circumferential surface of the first dancer roller R1, the webs W are passed through the first and third gaps Δ1 and Δ3. The webs W are reversed in direction by the reverse roll R3. The webs W are further passed through the fourth and second gaps Δ4 and Δ2 to the second dancer roller R2. After flown along the outer circumferential surface of the second dancer roller R2, the webs W are transported along the second guide roller G2 at a substantially constant speed V.

The first dancer roller R1 is moved in the direction of the arrow D20 so that the length of the webs W between the first dancer roller R1 and the first gap Δ1 is increased, whereas the second dancer roller R2 is moved in the direction of the arrow D20 so that the length of the webs W between the second dancer roller R2 and the second gap Δ2 is decreased.

In this way, the speed of the webs W between the first dancer roller R1 and the second dancer roller R2 is lower than the speed V of the webs W flowing into the first dancer roller R1.

When the webs W are transported at the low speed, the anvils 11 to 14 are respectively opposite to the ultrasonic horns 21 to 24, and the sonic main bodies 31 to 34 are operated, with the result that for example, the welded regions Sa3, Sa3 which are adjacent to each other in the webs W of FIG. 3(a) are simultaneously welded (sealed).

The first dancer roller R1 is moved in the direction of the arrow D10 so that the length of the webs W between the first dancer roller R1 and the first gap Δ1 in FIG. 1 is decreased, whereas the second dancer roller R2 is moved in the direction of the arrow D10 so that the length of the webs W between the second dancer roller R2 and the second gap Δ2 is increased.

In this way, the speed of the webs W between the first dancer roller R1 and the second dancer roller R2 is higher than the speed V of the webs W flowing into the first dancer roller R1.

With respect to the welding described above, as shown in FIG. 3(a), one welded region Sa3 may be welded twice with two or more of the ultrasonic horns 21 to 24.

In other words, when the four anvils 11 to 14 of FIG. 1 are respectively opposite to the four ultrasonic horns 21 to 24, the four ultrasonic horns 21 to 24 apply the vibration energy to a predetermined part (the welded region Sa3 of FIG. 3(a)) of the webs W. Thereafter, when the four anvils 11 to 14 are respectively opposite to the ultrasonic horns 21 to 24, the second to fourth ultrasonic horns 22 to 24 apply the vibration energy again to the predetermined part (the welded region Sa3) to which the vibration energy has been applied with the first ultrasonic horn 21.

As shown in FIG. 3(a), the welded region Sa3 forms an end portion of a product such as a wearing article.

In this case, the transport speed of the webs W and the angular speed of the anvil roll 10 are controlled so that the welded region Sa3 (FIG. 3(a)) welded in the first gap Δ1 of FIG. 1 with the first ultrasonic horn 21 is then welded in any one of the second to fourth gaps Δ2 to Δ4 with the ultrasonic horns 22 to 24.

In the welding described above, the vibration energy is applied to one place of the webs twice, and thus the reliability of the welding is enhanced.

On the other hand, as shown in FIG. 3(b), each of the welded regions Sa1 to Sa4 may be welded with only any one of the ultrasonic horns 21 to 24.

In this case, as shown in FIG. 3(b), the welded regions Sa1 to Sa4 welded with the first to fourth ultrasonic horns 21 to 24 repeatedly appear in the webs W.

An example thereof will be described below.

In FIG. 1, the first distance D1 between the first gap Δ1 and the third gap Δ3 as well as the first distance D1 between the fourth gap Δ4 and the second gap Δ2 are individually set at the length Spm of the medium size in FIG. 3(a).

On the other hand, the reverse roll R3 is attached to the frame 5 in the first position P1 such that a transport distance from the third gap Δ3 to the fourth gap Δ4 is five times as long as the first distance D1. In such an arrangement, the welding is performed as follows.

While as in FIGS. 4(a) to 4(d), the webs W are being transported with speed change so that the webs W are passed through the first gap Δ1, the third gap Δ3, the fourth gap Δ4, and the second gap Δ2 in this order, the first part S1 and the second part S2 of the webs W are ultrasonic-welded with the third and first horns 23 and 21 of FIG. 4(a), respectively, in low-speed transport.

Thereafter, as in FIG. 4(b), the webs W are transported at high speed by a length four times as long as the first distance D1, and then, the third part S3 and the fourth part S4 of the webs W on the downstream side with respect to the second part S2 are respectively ultrasonic-welded with the third and first horns 23 and 21 in low-speed transport.

In FIGS. 4(a) to 4(d), the parts of the webs W that are ultrasonic-welded are painted in black.

Thereafter, over again, as in FIG. 4(c), the webs W are transported at high speed by a length four times as long as the first distance D1, and then, the fifth part S5 and the sixth part S6 of the webs W between the second part S2 and the third part S3 described above are respectively ultrasonic-welded with the second and fourth horns 22 and 24 in low-speed transport.

Here, the seventh part S7 and the eighth part S8 of the webs W that are respectively opposite to the sixth part S6 and the fifth part S5 described above are ultrasonic-welded with the third and first horns 23 and 21 in the low-speed transport described above.

In other words, the timing at which the sixth part S6 and the fifth part S5 are ultrasonic-welded is the same as the timing at which the seventh part S7 and the eighth part S8 are ultrasonic-welded.

Thereafter, over again, the webs W are transported at high speed by a length four times as long as the first distance D1, and the ninth part S9 and the tenth part S10 of the webs W between the fourth part S4 and the seventh part S7 described above are ultrasonic-welded with the second and fourth horns 22 and 24.

Here, the eleventh part S11 and the twelfth part S12 of the webs W that are respectively opposite to the tenth part S10 and the ninth part S9 are ultrasonic-welded with the third and first horns 23 and 21 in the low-speed transport described above.

Note that when the first to fourth parts S1 to S4 are ultrasonic-welded the parts of the webs W that are respectively opposite to them through the anvil rolls are ultrasonic-welded. In order to make the description of the steps easy to understand, in FIGS. 4(a) to 4(b), the welded parts of the webs W opposite to the first to fourth parts S1 to S4 are not illustrated (not painted in black).

In this example, the time during which high-speed transport is performed is increased, and thus it is possible to further enhance the production speed.

A method of changing the size of the wearing article N from the medium size of FIG. 3(b) to the large size of FIG. 3(c) will then be described.

In the medium size of FIG. 3(b), the first and second anvil rolls 10A and 10B and the first to fourth sonic main bodies 31 to 34 are attached to the frame 5 so that the first distance D1 between the first gap Δ1 and the third gap Δ3 as well as the first distance D1 between the second gap Δ2 and the fourth gap Δ4 are equal to the product length Spm of FIG. 3(b).

On the other hand, the reverse roll R3 is attached to the frame 5 so that the length of the webs W from the third gap Δ3 to the fourth gap Δ4 is an integral multiple (for example, 5 times) of the first distance D1. In this state, as described above, the ultrasonic welding is intermittently performed, and thus it is possible to obtain the wearing article N of the medium size in FIG. 3(b).

On the other hand, when the wearing article N of the large size in FIG. 3(c) is manufactured, the first and second anvil rolls 10A and 10B and the first to fourth sonic main bodies 31 to 34 in FIG. 2 are attached to the frame 5 so that the first distance D1 is equal to the product length Spl of FIG. 3(c).

On the other hand, the reverse roll R3 is attached to the frame 5 so that the length of the webs W from the third gap Δ3 to the fourth gap Δ4 is an integral multiple (for example, 5 times) of the first distance D1. In this state, as described above, the ultrasonic welding is intermittently performed, and thus it is possible to obtain the wearing article N of the large size in FIG. 3(c).

The preferred embodiment has been described above with reference to the drawings, and the person skilled in the art may easily conceive various variations and changes within the obvious scope with reference to the present specification.

For example, the reverse roll and/or the speed change device not necessarily need to be provided.

The reverse roll may be provided such that its position is fixed.

In the method of changing the size of the wearing article, the reverse roll, the second anvil roll, and the third and fourth sonic main bodies may be moved along the long hole with power produced by a motor, a cylinder or the like. Furthermore, instead of the long hole, a guide member such as a linear guide may be used.

The reverse roll, the first anvil roll, the second anvil roll, and the sonic main bodies may have a means in the first and second positions that can finely adjust the positions.

The dancer roller may swing not vertically but laterally.

Hence, such variations and changes are interpreted to fall within the scope of the present invention defined by the scope of claims.

INDUSTRIAL APPLICABILITY

The welding system of the present invention can be utilized in the production of disposable wearing articles such as disposable pants, diapers and sanitary napkins.

REFERENCE SIGNS LIST 1, 2: first and second ultrasonic welding devices 10A: first anvil roll, 10B: second anvil roll, 11 to 14: first to fourth anvils
21 to 24: first to fourth ultrasonic horns
31 to 34: first to fourth sonic main bodies
4: transport device, 41, 42: first and second size adjustment means
5: frame, 50: attachment unit, 51: long hole
N: wearing article, P1: first position, P2: second position
R1: first dancer roller, R2: second dancer roller
R3: reverse roll, R4: drive roller
S1 to S10: first to tenth parts, Sa1 to Sa4: welded regions
Δ1 to Δ4: first to fourth gaps

The invention claimed is:

1. A web welding system including an ultrasonic welding device that welds a plurality of webs together while the system transferring the webs, the ultrasonic welding device comprising:
   a first anvil roll that includes a pair of anvils;
   first and second ultrasonic horns that work together with the pair of anvils to apply vibration energies to the webs;
   a second anvil roll that includes another pair of anvils; and
   third and fourth ultrasonic horns that work together with the pair of anvils in the second anvil roll to apply vibration energies to the webs,
   wherein the first and second ultrasonic horns are arranged so that when any one of the pair of anvils in the first anvil roll is opposed to the first horn, another of the pair of anvils in the first anvil roll is simultaneously opposed to the second horn,
   the third and fourth ultrasonic horns are arranged so that when any one of the pair of anvils in the second anvil roll is opposed to the third horn, another of the pair of anvils in the second anvil roll is simultaneously opposed to the fourth horn, and
   the first and second anvil rolls are arranged so that the webs are transferred to pass through, in sequence, a first gap between the first anvil roll and the first horn, a third gap between the second anvil roll and the third horn, a fourth gap between the second anvil roll and the fourth horn, and a second gap between the first anvil roll and the second horn.

2. The system according to claim 1, further including:
   a first size adjustment means that adjusts a first distance between the first anvil roll and the second anvil roll.

3. The system according to claim 2, further including:
a reverse roll that is arranged on a side of the second anvil roll opposite to the first anvil roll and that reverses a direction of the webs passing through the third gap toward the fourth gap; and
a second size adjustment means that adjusts a second distance between the second anvil roll and the reverse roll.

4. The system according to claim 3,
wherein the pair of anvils in the first anvil roll are provided symmetrically with respect to an axis line of the first anvil roll, and
the pair of anvils in the second anvil roll are provided symmetrically with respect to an axis line of the second anvil roll.

5. A method of welding webs using the system according to claim 1, the method comprising:
a step of transferring the webs so that the webs pass through, in sequence, the first gap, the third gap, the fourth gap, and the second gap;
a step of ultrasonic-welding a first part and a second part of the webs with the third horn and the first horn, respectively;
a step of ultrasonic-welding a third part and a fourth part of the webs with the third horn and the first horn, respectively, on a downstream side with respect to the second part; and
a step of ultrasonic-welding a fifth part and a sixth part of the webs with the second horn and the fourth horn, respectively, between the second part and the third part.

6. The method of welding webs according to claim 5,
wherein the welding system further comprises a transfer device that introduces the webs into the first gap and receives the webs from the second gap, and that repeatedly performs high-speed transfer and low-speed transfer of the webs in a predetermined period,
the welding method further comprises a step of repeatedly performing the high-speed transfer of the webs and the low-speed transfer of the webs with assumption that a length four times as long as a pitch of weldings determined by a first distance between the first gap and the third gap is one period, and
the ultrasonic-welding steps are performed when the low-speed transfer is performed.

* * * * *